US006048528A

United States Patent [19]
Dunbar

[11] Patent Number: 6,048,528
[45] Date of Patent: Apr. 11, 2000

[54] MONOCLONAL ANTIBODY FOR DIAGNOSTIC AND THERAPEUTIC USE IN OVARIAN CANCER

[75] Inventor: Bonita S. Dunbar, Houston, Tex.

[73] Assignee: Baylor College of Medicine, Houston, Tex.

[21] Appl. No.: 08/977,373

[22] Filed: Nov. 24, 1997

Related U.S. Application Data

[60] Continuation of application No. 08/520,584, Aug. 29, 1995, abandoned, which is a division of application No. 08/326,053, Oct. 19, 1994, Pat. No. 5,484,704, which is a continuation of application No. 07/975,093, Nov. 12, 1992, abandoned.

[51] Int. Cl.$^7$ .......................... A61K 39/395; C07K 16/00
[52] U.S. Cl. .................................... 424/178.1; 424/183.1; 530/391.7
[58] Field of Search .............................. 424/178.1, 184.1, 424/183.1, 193.1, 277.1; 435/7.23, 344; 530/387.7, 389.7, 391.3, 391.7

[56] References Cited

U.S. PATENT DOCUMENTS

| | | | |
|---|---|---|---|
| 4,650,756 | 3/1987 | Old | 435/68 |
| 4,666,845 | 5/1987 | Mattes | 435/172.2 |
| 4,695,538 | 9/1987 | Cote | 435/172.2 |
| 4,713,351 | 12/1987 | Knauf | 436/542 |
| 4,725,538 | 2/1988 | Senger | 435/29 |
| 4,806,494 | 2/1989 | Pastan et al. | 424/85.91 |
| 4,814,275 | 3/1989 | Durda | 435/240.27 |
| 4,857,452 | 8/1989 | Ho | 435/172.2 |
| 4,921,790 | 5/1990 | O'Brien | 435/172.2 |
| 5,094,942 | 3/1992 | Hashizume | 435/7.23 |

OTHER PUBLICATIONS

Lidor et al. "Serotherapy of Ovarian Cancer" Natural Immunity and Cell Growth Regulation. vol. 7 No. 4, pp. 193–215, 1988.
Anderson, *J. Morphol.*, 150:135–164 (1976).
Blaustein, *Gynecol.*, 8:34–43 (1979).
Cantarow, *Int. J. Radiation Oncol. Biol. Phys.*, 7:1095–1098 (1981).
Duffy, *Ann. Clin. Biochem.*, 26:379–387 (1989).
Dunbar, In: Two Dimensional Gel Electrophoreses and Immunological Techniques, Plenum Press, New York, pp. 223–225 (1987).
Dunbar, In: Proceedings Int'l. Conference on Reprod. Immuno., T. Gill and T. Wegman, eds., Oxford University Press, pp. 505–535.
East, *J. Cell. Biol.*, 98:795–800 (1984).
Kenemans, *Eur. J. Obst. Gynecol. Reprod. Biol.*, 29:207–218 (1989).
Kudlacek, *Gyn. Onc.*, 35:323–329 (1989).
Larrick et al, *Human Antibodies and Hybridomas*, 2:172–189 (1991).
Maresch et al, *Biol. Reprod.*, 43:965–976 (1990).
Nicosia, *Int. J. Gynecol. Pathol.*, 3:249–260 (1983).
Nicosia, *Int. J. Gynecol. Pathol.*, 3:348–360 (1983).
Omar et al, *Tumor Biol.*, 10:316–323 (1989).
Papadaki, *J. Cell Science*, 8:445–464 (1971).
Rustin, *J. Clin. Onc.*, 7:1667–1671 (1989).
Sevelda, *Am. J. Obstet. Gynec.*, 161:1213–1216 (1989).
Siemens, *J. Cellular Physiol.*, 134:347–356 (1988).
Skinner, *J. Histochem. Cytochem.*, 40:1031–1036 (1992).
Timmons, In: Perspectives in Immunoreproduction: Conception and Contraception, Mather and Fredericks, eds, Hemisphere Press, New York, p. 242 (1988).
Timmons, *Biol. Reprod.*, 36:1275 (1987).
Harris et al, *TIBTECH*, 11:42–44 (1993).
McGuckin et al, *J. Tumor Marker Oncol.*, 5(1):87–94 (1990).
Stedmans' Medical Dictionary, Waverly Press, 24th Edition, pp. 546 and 1008 (1984).

*Primary Examiner*—Yvonne Eyler
*Attorney, Agent, or Firm*—Sughrue, Mion, Zinn, Macpeak & Seas, PLLC

[57] ABSTRACT

A method for the diagnosis and treatment of ovarian cancer. Tissue and body fluid samples are assayed for an antigen which specifically binds an anti-OSE antigen to diagnose ovarian cancer. Therapeutic agents coupled to anti-OSE antibodies, such as PS1 are specifically directed to ovarian cancer tissues.

1 Claim, 7 Drawing Sheets

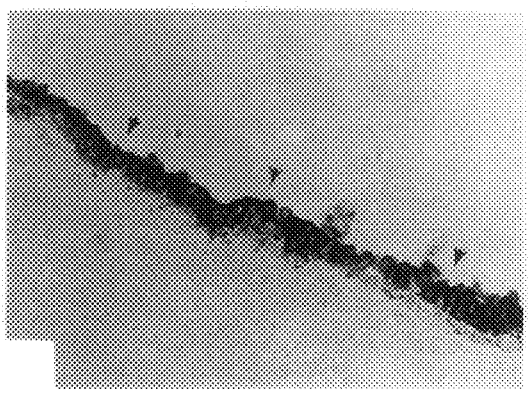
FIG. IA
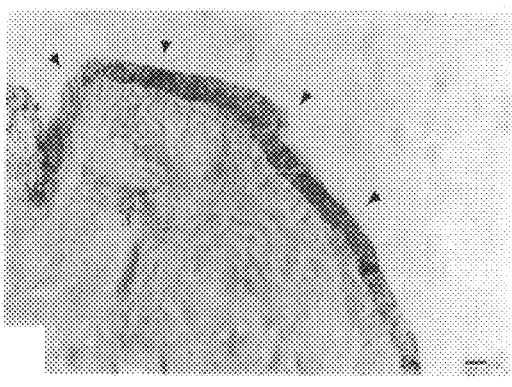
FIG. ID
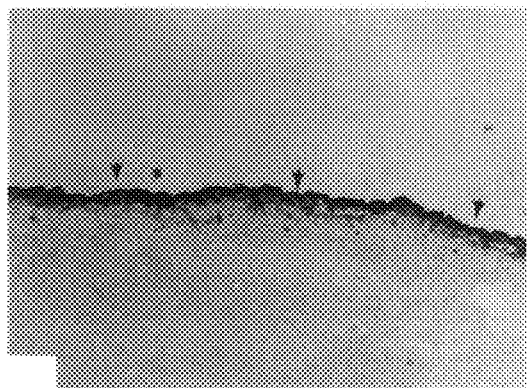
FIG. IB
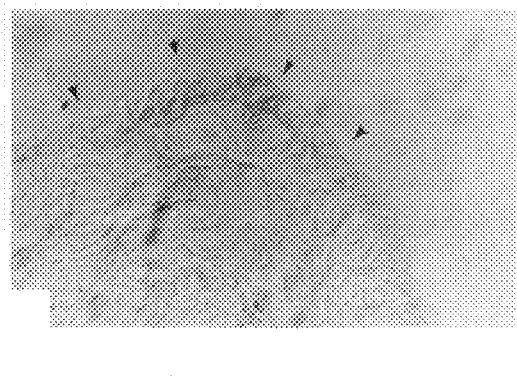
FIG. IE
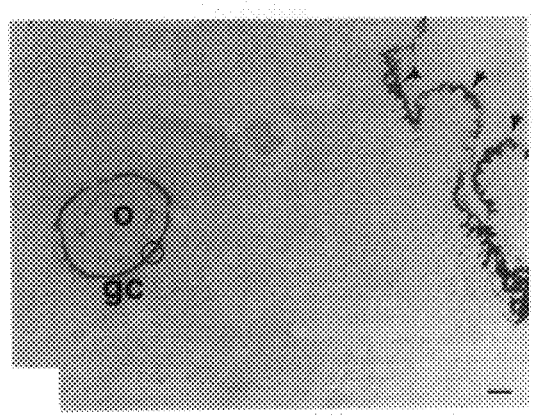
FIG. IC

MONOCLONAL ANTIBODY FOR DIAGNOSTIC AND THERAPEUTIC USE IN OVARIAN CANCER

This is a Continuation of Parent application Ser. No. 08/520,584 now abandoned, filed on Aug. 29, 1995; which in turn is a Divisional of application Ser. No. 08/326,053, filed Oct. 19, 1994 (now U.S. Pat. No. 5,484,704); which in turn is a Continuation of application Ser. No. 07/975,093, filed Nov. 12, 1992 (now abandoned).

FIELD OF THE INVENTION

The present invention relates to a method for the detection, monitoring, and treatment of ovarian cancer. More specifically, this invention relates to the use of a monoclonal antibody which specifically recognizes an ovarian antigen secreted by the ovarian surface epithelium.

BACKGROUND OF THE INVENTION

Cancer of the ovary is the second most common cancer of the female reproductive organs and the fourth most common cause of cancer deaths among American women. Because ovarian cancers are not readily detectable by diagnostic techniques (Siemens and Auersperg, 1988, J. Cellular Physiol., 134:347–356). Because diagnosis of carcinoma of the ovary is generally only possible when the disease has progressed to a late stage of development, it is one of the most lethal of the gynecological malignancies.

There is a vital need for the identification of tumor markers which can be used in the early detection of ovarian cancer, the monitoring of cancer therapies, the immunodetection of ovarian tumors, and the development of probes for potential use in immunotherapy (Cantarow et al., 1981, Int. J. Radiation Oncol. Biol. Phys., 7:1095–1098). Although a number of potential tumor markers have been evaluated including the cancer antigen 125 (Ca-125) nonspecificity of the antigens diminish their value as markers for primary ovarian cancer (Kudlacek et al., 1989, Gyn. Onc., 35:323–329; Rustin et al., 1989, J. Clin. Onc., 7:1667–1671; Sevelda et al., 1989, Am. J. Obstet. Gynecol., 161:1213–1216; Omar et al., 1989, Tumor Biol., 10:316–323).

Several monoclonal antibodies have recently been shown to react with ovarian tumor associated antigens (Kenemans et al., 1989, Eur. J. Obstet. Gynecol. Repod. Biol., 29:207–218). These antibodies do not appear to be specific to a specific type of cancer (McDuffy, 1989, Ann. Clin. Biochen., 26:379–387). Many of these antibodies recognize determinants associated with high molecular weight glycoproteins related to mucins. Additional markers such as enzymes or activated cellular oncagenes or products of these genes have also been suggested for use as ovarian cancer markers. These potential probes, however, have not been detected in the blood and hence their use is confined to analysis of tumor tissues.

The majority, e.g., 80–90%, of ovarian cancers are thought to arise from the ovarian surface of epithelium (OSE). To date, little is known about the structure and function of the cells of the ovarian surface epithelium. It is known that the surface epithelium is a highly dynamic tissue which undergoes morphogenic changes. The OSE also has significant proliferative properties, as it it must proliferate rapidly to cover the ovulatory site after ovulation of the ova. Morphological and histochemical studies suggest that the OSE has secretory, endocytotic and transport functions which are hormonally controlled (Blaustein and Lee, 1979, Oncol. 8:34–43; Nicosia and Johnson, 1983, Int. J. Gynecol. Pathol., 3:249–260; Papadaki and Beilby, 1971, J. Cell Sci., 8:445–464; Anderson et al., 1976, J. Morphol., 150:135–164).

There is a vital need for an ovarian cancer marker which can specifically detect ovarian cancer, which marker can be used to diagnose, monitor and identify ovarian cancers and which may be used in specific immunotherapy.

SUMMARY OF THE INVENTION

The present invention provides a method for the specific detection, monitoring, and/or treatment of ovarian cancer. In the method of the present invention, an in vitro assay employs antibodies which specifically recognize an antigen of the ovarian surface epithelium (OSE) to determine the presence and amounts of OSE antigen in tissues or body fluids of patients. Such assay permits detection of ovarian cancer, monitoring of ovarian cancers and specific identification of ovarian cancer type. Anti-OSE antibodies are also used to specifically target therapeutic agents to ovarian cancer cells.

For diagnosing and classifying ovarian cancer types, ovarian cancer tissues are probed with an anti-OSE antibody, e.g., by immunohistochemical methods. For detection and monitoring of ovarian cancer in body fluids, the anti-OSE antibodies are preferably used in immunoassays to detect a secreted OSE antigen. For therapeutic purposes, anti-OSE antibodies conjugated to cytotoxic agents are administered for targeted delivery to OSE antigens present in the ovarian cancer.

BRIEF DESCRIPTION OF THE FIGURES

FIG. 1 shows localization of PS1 antigen in OSE of cynamologous monkeys (FIG. 1A), baboons (FIG. 1B), rabbit (FIG. 1C) and human (FIG. 1D). FIG. 1E shows a section of human ovary probed with control, anti-myeloma antibody. Arrows indicate ovarian surface epithelium.

FIG. 2 shows histological sections of paraffin embedded human ovarian tumors.

FIG. 3 shows histological sections of paraffin embedded normal human ovaries.

FIG. 4 shows histological sections of a paraffin embedded Brenners tumor.

DETAILED DESCRIPTION OF THE INVENTION

Figure 2A:
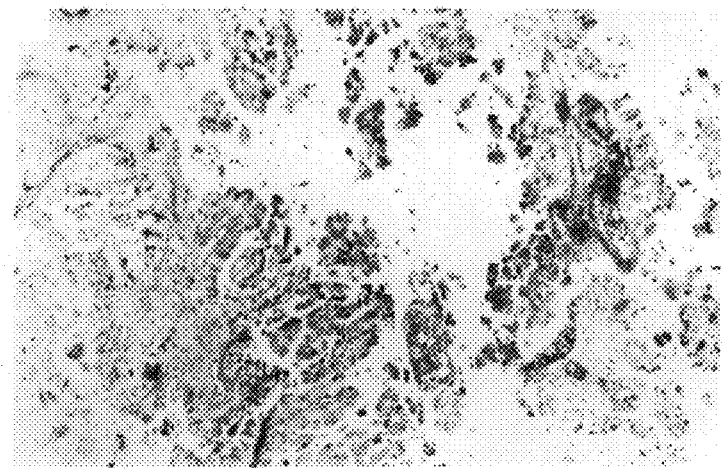
FIG. 2A shows sample 13022 stained with PAS.
Figure 2B:
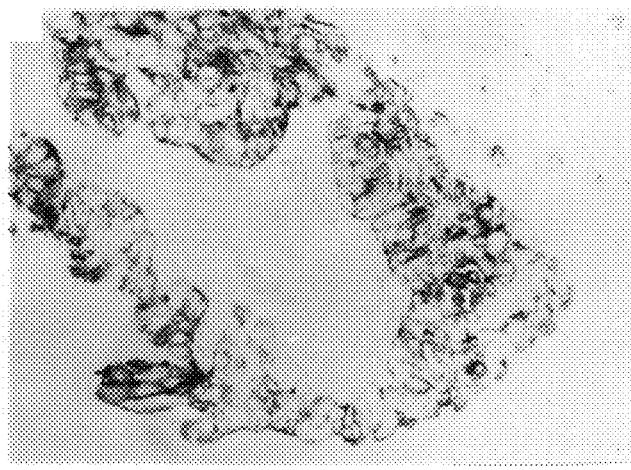
FIG. 2B shows sample 13022 reacted with PS1 antibody.
Figure 2C:
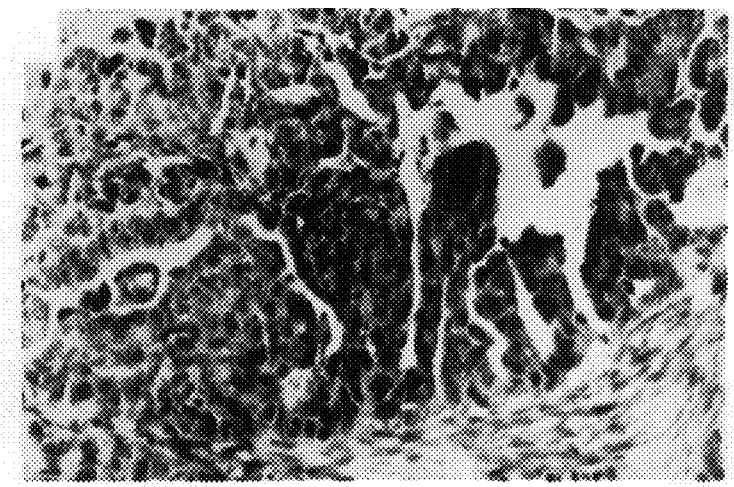
FIG. 2C shows sample 9010 stained with PAS.
Figure 2D:
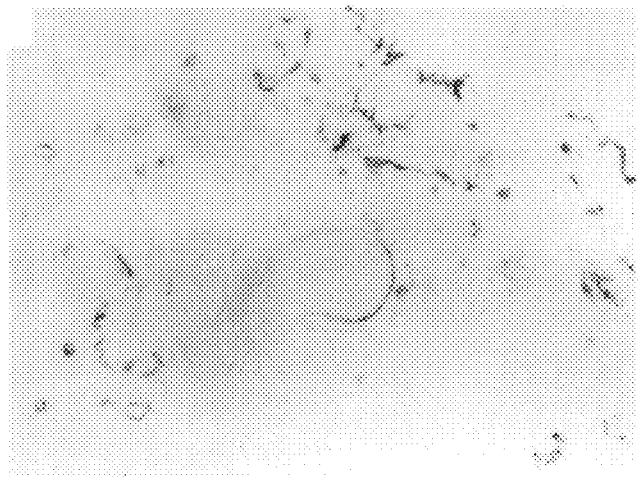
FIG. 2D shows sample 9010 reacted with PS1 antibody.
Figure 2E:
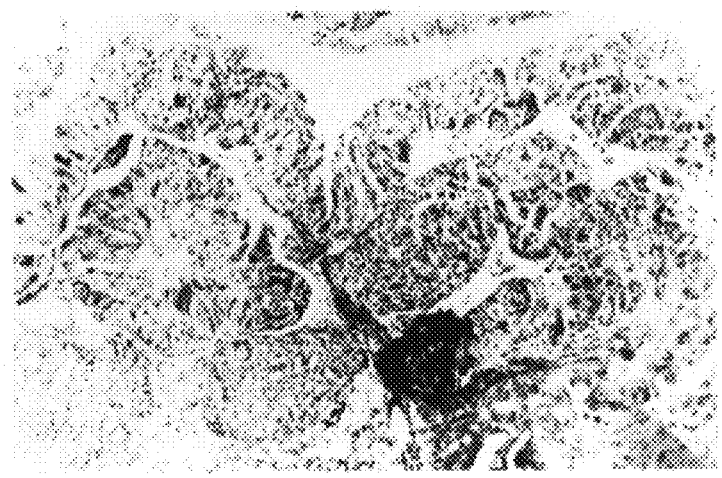
FIG. 2E shows sample 10035 stained with PAS.
Figure 2F:
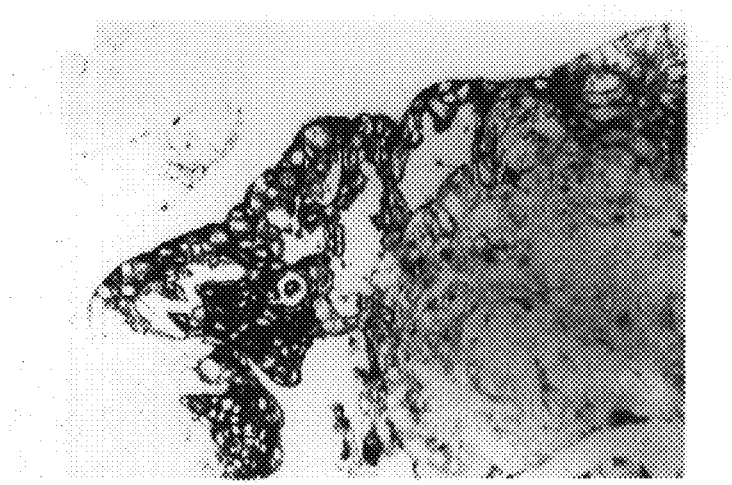
FIG. 2F shows sample 10035 reacted with PS1 antibody.
Figure 2G:
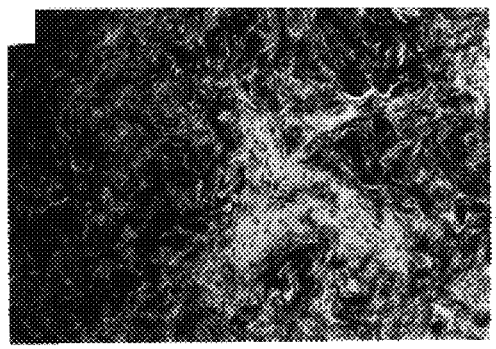
FIG. 2G shows sample 13017 stained with PAS.
Figure 2H:
FIG. 2H shows sample 13017 reacted with PS1 antibody.
Figure 2I:
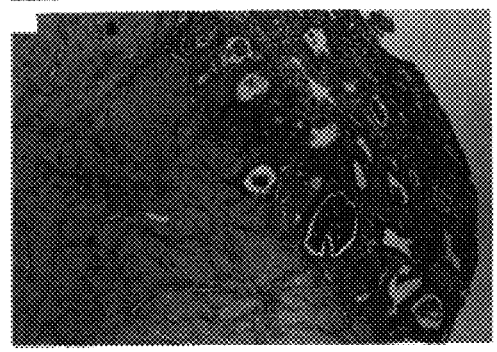
FIG. 2I shows sample 9160 stained with PAS.
Figure 2J:
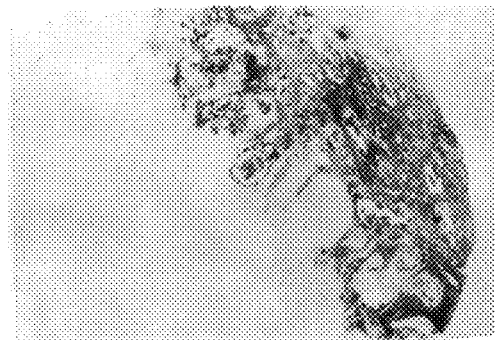
FIG. 2J shows sample 9160 stained with PS1 antibody.
Figure 2K:
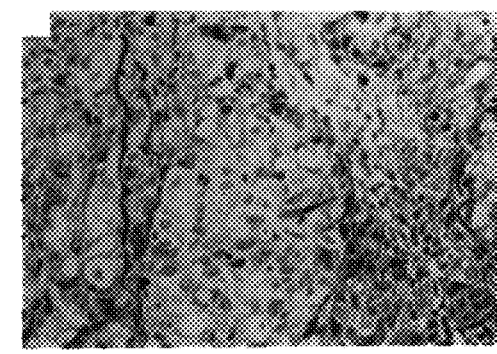
FIG. 2K shows sample 10880 stained with PAS.
Figure 2L:
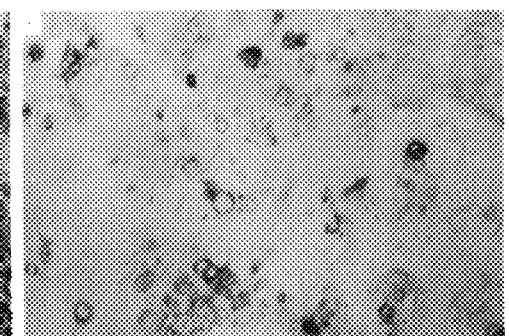
FIG. 2L shows sample 10880 reacted with PS1 antibody.
Figure 2M:
FIG. 2M shows sample 9219 stained with PAS.

In the method of the present invention, antibodies which specifically recognize antigens of the ovarian surface epithelium are used as diagnostic or therapeutic tools to determine the presence and amounts of OSE antigen in the tissues or blood of patients to diagnose, identify, and monitor ovarian cancer. In an alternative embodiment anti-OSE antibodies are used to specifically target therapeutic agents to tissues expressing OSE antigens, e.g., ovarian cancer tissues.

The antibodies used in the method invention specifically bind antigens of the ovarian surface epithelium, and also recognize antigens present in the cell surface membranes and preferably for diagnosis, antigens secreted by these epithelial cells.

For diagnosing and classifying ovarian cancer types, the anti-OSE antibodies preferably bind ovarian cancer tissues. For detection of ovarian cancer in body fluids such as blood, peritoneal fluid, tissue fluid, and the like, the anti-OSE antibodies preferably bind antigens secreted by the OSE and by the ovarian cancer cells. For therapeutic purposes, the anti-OSE antibodies preferably bind antigens associated with the cell surface membranes of the ovarian cancer, and thereby deliver therapeutic agents to the tumor.

Antibodies useful in the present invention may be polyclonal, monoclonal, or recombinant antibodies, and are prepared by methods generally known in the art. See, for example, Dunbar, 1987, *Two Dimensional Gel Electrophoresis and Immunological Techniques*, Plenum Press, New York, and Larrick and Fry, 1991, *Human Antibodies and Hybridomas*, 2:172–189.

Antigens which may be used to produce antibodies useful in the method invention are those present in the ovarian surface epithelium (OSE) and those antigens secreted by the OSE. The antigens may be, for example, a protein, a glycoprotein, or a carbohydrate moiety.

Antibodies to be used in the method invention are those which specifically bind normal OSE and those which specifically bind an antigen secreted by normal OSE, and also specifically bind ovarian cancer cells or antigens secreted by ovarian cancer cells.

The phrases "specifically binds" and "having specificity for" are meant to include binding of the anti-OSE antibody to ovarian tissues and to ovarian cancer cells with little or no binding to non-ovarian tissues or cancers of non-ovarian origin.

For example, the monoclonal antibody PS1 described by Tivnons and Dunbar (1988, in Mathur and Fredericks, eds., *Perspectives in Immunoreproduction: Conception and Contraception*, Hemisphere Press, New York, p. 242) has surprisingly been found to recognize an antigen present in the ovarian surface epithelium of cynomolgus monkey, baboon, rabbit, and human ovarian tissues. PS1 also binds an antigen secreted by ovarian cell surface epithelium, in vitro, and specifically recognizes an ovarian cancer antigen.

The PS1 antibody has been previously described as recognizing a ovarian zona pellucida antigen, and has been characterized as recognizing a carbohydrate constituent of this antigen (Timmons et al., 1987, *Biol. Reprod.*, 36:1275). The PS1 monoclonal antibody has been found to localize not only to the oocyte and its surrounding extracellular matrix but also in the secretory, apical portion of the ovarian surface epithelium.

PS1 specifically binds ovarian tumor tissue and can be used to distinguish ovarian cancer cells from non-carcinogenic tissue for diagnostic purposes and for the classification of tumor types based upon histological sections and immunohistochemical assays.

When the antibody PS1 is used in immunohistochemical assays of human cancer tissues, the antibody specifically binds throughout the ovarian cancer tissue while showing no significant binding to non-ovarian cancer types. Normal ovaries show binding of the antibody in the remnants of the OSE.

The hybridoma cell line which produces monoclonal antibody PS1 was deposited under the provisions of the Budapest Treaty and accepted by the American Type Culture Collection (ATCC), 10801 University Boulevard, Manassas, Va. 20110-2209, on Oct. 8, 1987, and given the accession number HB9565.

Metastatic ovarian cancer present in non-ovarian tissues may be identified using the method of the present invention. Thus, antibodies which specifically recognize antigens of the OSE are used to identify ovarian cancer tissue. The identified ovarian cancer tissue may be metastatic ovarian cancer cells present in non-ovarian tissues.

Preferably, the tissue to be assayed will be obtained by surgical procedures, e.g., biopsy. The excised tissue will be assayed for the presence of an antigen which recognizes an anti-OSE antibody as described above, e.g., PS1, by methods generally known in the art, e.g., imunohistochemistry. The tissue may be fixed or frozen to permit histological sectioning, and may be stained prior to incubation with the antibody. The antibody may be labeled, for example with a dye or fluorescent label, chemical, heavy metal or radioactive marker to permit the detection and localization of the antibody in the assayed tissue. Alternatively, other immunological assays known to those of skill in the art may be employed which permit detection of antibody binding to the excised tissue.

Because the PS1 antigen is a carbohydrate moiety, and has now been found to be a secretory antigen in the oocyte, secretion of the PS1-recognized antigen by OSE provides a specific ovarian cancer marker for detection in body fluids of patients presenting with proliferation of this cell type, e.g., ovarian cancer. Additional antigens secreted by the OSE may be used to prepare antibodies which, like PS1, may be used to diagnose ovarian cancer by immunoassay of tissue and body fluids for the presence of an antigen present in or secreted by ovarian cancer cells and recognized by the anti-OSE antibody.

Body fluids such as blood and fluid blood components, peritoneal fluid, tissue and the like may be assayed for the presence and amount of antigen which binds anti-OSE antibodies. The assay may be performed by methods routinely used by those of skill in the art. Generally, a sample of body fluid is added to an assay mixture containing the antibody and a marker system for detection of antigen-bound antibody. Examples of such immunoassay systems are radioimmunoassays (RIA), enzyme-linked immunoassays (ELISA), immobilized immunoassays, and the like.

Therapeutic agents useful in the treatment of ovarian cancer may be conjugated to the anti-OSE antibodies by methods known to those of skill in the art. Examples of such therapeutic agents include radioisotopes such as $^{131}$I or $^{67}$Cu and cytotoxic agents such as ricin or diphtheria toxin. $^{131}$I can be covalently bound to antibody molecules by methods known in the art, e.g., Iodogen® reactions. $^{67}$Cu may be attached by way of an appropriate metal chelator bound to the antibody. The toxins may be conjugated to antibodies by agents such as glutaraldehyde or carbodiimide.

Administration of the conjugated therapeutic agent-antibody may be by various means known in the art, but generally will be by injection, systemic or intraperitoneal and in a pharmaceutically acceptable carrier. A useful therapeutic dose will vary with the particular therapeutic agent used, the particular cancer type and history, and the specific considerations of the patient to be treated. A physician administering the agent will know to calculate the effective therapeutic dose, which dose will be effective in reducing or eliminating the tumor tissue without compromising significantly normal tissues of the patient.

The nature of the invention can be further understood by reference to the following examples.

EXAMPLE 1

IDENTIFICATION OF PS1 DETERMINANT IN OVARIAN SURFACE EPITHELIUM

Initial immunohistochemical localization studies demonstrated that the PS1 monoclonal antibody localized not only to the oocyte and surrounding extracellular matrix of the zona pellucida but also localized intensively in the secretory, apical portion of the ovarian surface epithelium.

Human and cat ovarian tissue was embedded and immediately frozen in OCT compound (Miles, Elkhart, Ind.). Cryostat sections, 4–8 µm were prepared using a Minotome/microtome cryostat, and the sections were fixed in 100% methanol for 10 minutes, blocked in TRIS-buffered saline (TBS), pH 7.5, containing 2.5% w/v Brij-35 (SIGMA, St. Louis, Mo.) and 6% w/v Carnation non-fat dried milk. Blocking-proceeded for thirty minutes at 37° C. in a moist chamber and was followed by brief rinsing in TBS/Brij.

The blocked sections were next incubated with the monoclonal antibody PS1 in a moist chamber for 30 minutes at 37° C. PS1 antibody was prepared as described in Timmons and Dunbar, 1988, in Mathur and Fredericks, eds., *Perspectives in Immunoreproduction: Conception and Contraception*, Hemisphere Press, New York, p. 242. Control sections were treated with IgG isolated from myeloma cell acetous fluid. The incubation was followed by rinsing in TBS/Brij and application of secondary antibody under the same conditions. The secondary antibody, peroxidase-labeled rabbit anti-mouse IgG (Dako, Santa Barbara, Calif.) was diluted 1:50 in blocking solution before application and was followed by washing in TBS and subsequent treatment with a solution of 3,3'-diaminobenzidine (Fisher Scientific, Fairlawn, N.J.) consisting of 50 mg freebase/100 ml TBS containing 0.0031% hydrogen peroxide at room temperature.

Rabbit and cynomolgus monkey ovarian tissue was similarly prepared and treated. Morphology was improved by finely mincing the rabbit tissues, fixing in 1% glutaraldehyde for one hour at room temperature, washing several times in chilled PBS, dehydration, and imbedding in Epon according to the manufacturer's instructions. Plastic embedment was followed by sectioning at 1–3 µm on a Mt-2 ultra microtome (Sorvall). Mounted sections were briefly etched (15 minutes) in sodium ethoxide/ethanol (1:1) and light trypsination (2.5% sucrose treatment followed by incubation in 0.0001% trypsin for 30 minutes at 37° C.). The blocking, antibody treatment, and signal development were performed as described above for human and cat ovarian tissue.

As shown in FIGS. 1A–1E, the PS1 antigenic determinant was localized in the ovarian surface epithelium of cynomolgus monkey (FIG. 11A), baboon (FIG. 1B), rabbit (FIG. 1C), and human (FIG. 1D) with intense localization on the apical portion of OSE (arrows). In contrast, the control myeloma antibody did not recognize human surface epithelium (FIG. 1E).

EXAMPLE 2

IDENTIFICATION OF PS1 DETERMINANT IN HUMAN OVARIAN CANCER TISSUE

Human ovarian tissue, both normal controls and tumor tissues were obtained as fixed sections embedded in paraffin from the Department of Pathology, M.D. Anderson Hospital, Houston, Tex. Immunohistochemical assay of the sections was performed as follows:

Paraffin was first removed and the sections rehydrated by six (6) minute washes, in each of Xylene (twice), 100% ethanol (twice), 95% ethanol, 85% ethanol, 70% ethanol, 50% ethanol, and distilled, deionized water. The sections were next incubated 15–20 minutes in 3% hydrogen peroxide in methanol and washed 3 times in PBS containing 0.1% BSA, 5 minutes per wash. The washed sections were next blocked by incubating 20 minutes with normal rabbit serum (diluted 1:500) in a humidified chamber at room temperature, and washed 3 times in PBS containing 0,1% BSA, 5 minutes per wash. The blocked sections were then incubated with PS1 IgG (1:500) or control antibody, IgG derived from ascites fluid of mice injected with p3U1 myeloma cells (Drell & Dunbar (1984) *Diolopy of Reproduction*, 30:445–457) (1:500) for two hours at room temperature, or overnight at 4° C., followed by three PBS washes as described above. Second antibody was applied by incubating with biotinylated rabbit anti-mouse IgG (Vectastain, Vector Laboratories, Burlingame, Calif.) for thirty (30) minutes at room temperature, followed by three PBS washes as described above. The sections were next incubated 30 minutes at room temperature with the avidin biotinylated horseradish/peroxidase reagent (ABC) (Vectastain) and washed three times in PBS as described above.

To stain the sections, 2 drops of 3% $H_2O_2$ was added to diaminobenzldine tetrahydrochloride DAB solution (3–5 mg/10 ml 0.1 M TRIS) iimediately before use. The sections were incubated with the prepared DAB solution for 5–10 minutes, washed twice in dd $H_2O$, and coverslips applied.

The assayed sections were then viewed by light microscopy. Sections of "normal" human ovarian tissue (ovarian tissue having no gross pathology as evaluated by M.D. Anderson pathologists) was compared with sections of tissue surgically removed from cancer patients.

Figure 2N:
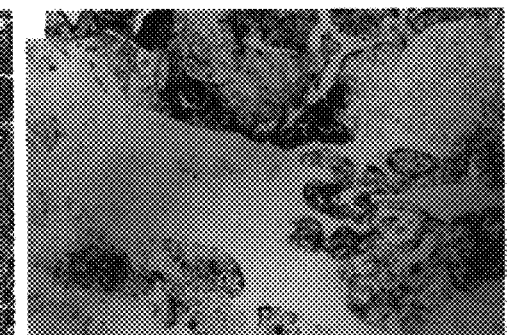
FIG. 2N shows sample 9219 reacted with PS1 antibody.
Figure 3A:
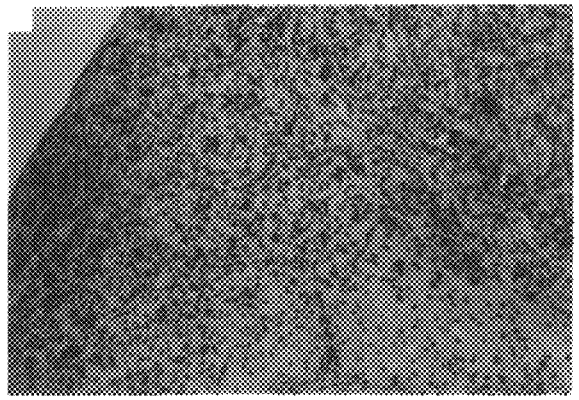
FIG. 3A shows sample 13053 stained with PAS.
Figure 3B:
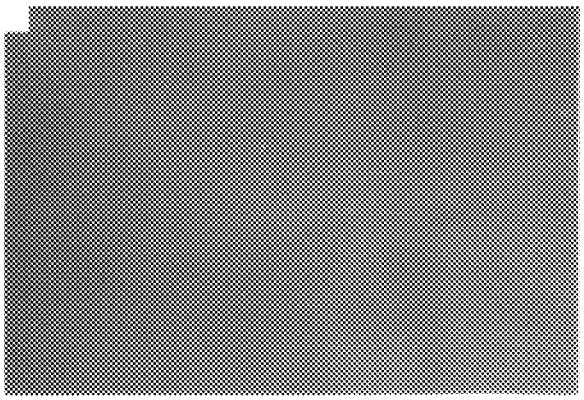
FIG. 3B shows sample 13053 reacted with PS1 antibody.
Figure 3C:
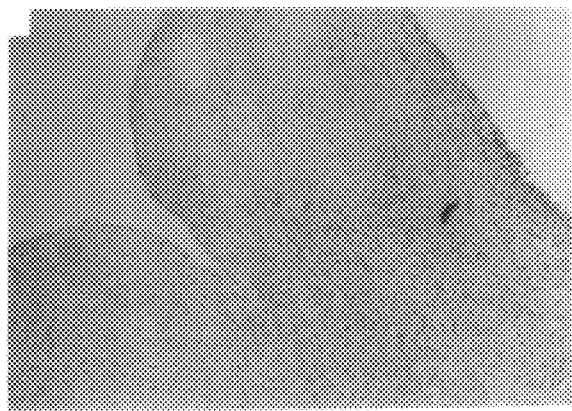
FIG. 3C shows sample 13012 stained with PAS.
Figure 3D:
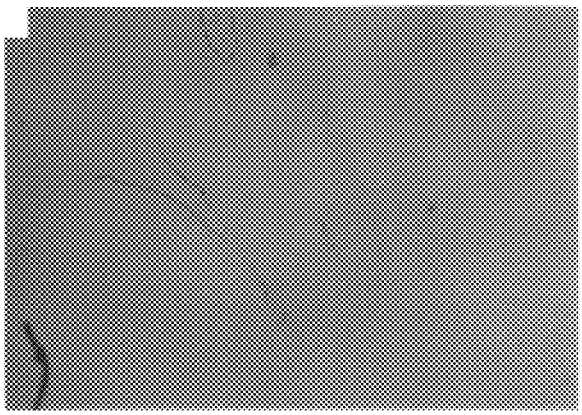
FIG. 3D shows sample 13012 reacted with PS1 antibody.
Figure 4A:
FIG. 4A shows sample 13044 stained with PAS.
Figure 4B:
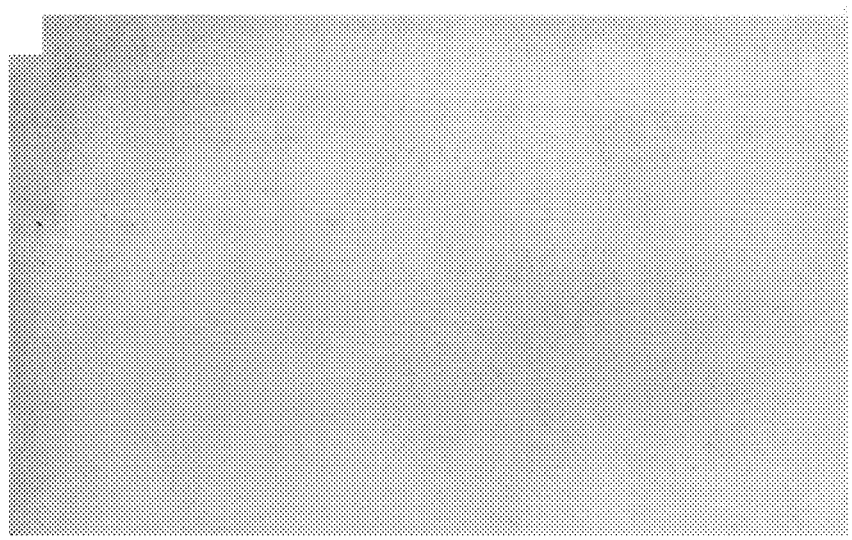
FIG. 4B shows sample 13044 reacted with PS1 antibody.

As shown in FIGS. 2, 3 and 4, the monoclonal antibody PS1 specifically recognized an antigen present in human ovarian tumors (FIGS. 2A–2N). In contrast, antibody specific antigen was identified only in the remnant ovarian cell surface epithelium of normal, adult ovarian tissues (FIGS. 3A–3D). FIGS. 4A and B show histological sections of a Brenner's tumor. This tumor is generally considered to be non-malignant and does not react with the PS1 antibody, which specifically identifies ovarian malignancies derived from OSE. Histological data for these and additional human tissue samples is summarized in Table 1.

TABLE 1

| SAMPLE NO. | TISSUE | DIAGNOSIS | PS1 PRESENCE[b] (Localization) |
|---|---|---|---|
| 13012 | OVARY | NORMAL | RESIDUAL OSE ONLY (IN CRYPTS) |
| 13057 | OVARY | NORMAL | + Residual OSE |
| 13053 | OVARY | NORMAL | – |
| 13018 | OVARY | NORMAL | – |
| 13004 | OVARY | NORMAL | – |
| 13065 | OVARY | NORMAL | – |
| 9213 | OVARY | NORMAL | – |
| 13017 | OVARY | ADENOCARCINOMA OF ENDOMETRIUM | + |
| 13078 | OVARIAN TUMOR | PAPILLARY SEROUS CARCINOMA | ++ |
| 9129 | OVARIAN TUMOR | BRENNER'S MUCINOUS TUMOR METASTATIC ADENOCARCINOMA OF LIVER | + (FEW ISOLATED EPITHELIAL CELLS) |
| 13022 | OVARIAN TUMOR | PAPILLARY SEROUS | +++ |
| 9208 | OVARIAN TUMOR | TERATOMA TUMOR | ++ |
| 13027 | OVARIAN TUMOR | SEROUS CYST | + |
| 9010 | OVARIAN TUMOR | SEROUS METASTATIC | ++ |
| 13044 | OVARIAN TUMOR | BRENNER'S TUMOR | – |
| 13028 | OVARIAN TUMOR | GRANULOSA CELL TUMOR (RESEMBLES PAPILLARY SEROUS) | +++ |
| 10880 | OVARIAN TUMOR | SEROUS CARCINOMA | +++ |
| 1068 | OVARIAN TUMOR | METASTATIC TRANSITIONAL | +/– (SMALL POCKETS) |
| 9160 | OVARIAN TUMOR | ADENOCARCINOMA OF ENDOMETRIUM | +++ |
| 13023 | OVARIAN TUMOR | MATURE CYSTIC TERATOMA | – |
| 9219 | OVARIAN TUMOR | ENDOMETRIUM CARCINOMA OF OVARY WITH METASTATIC ADENOCARCINOMA | ++ |
| 10890 | OVARIAN TUMOR | MUCINOUS CYSTIC | ++ |
| 4703 | OVARIAN TUMOR | PAPILLARY SEROUS | ++ |
| 10035 | OVARIAN TUMOR | PAPILLARY SEROUS | ++ |

[a]Classification and tumor diagnosis by pathologists from M.D. Anderson Cancer Institute (Houston, TX)
[b]Monoclonal antibody PS1 localization: + = few cells but distinct; ++ = more general localization; +++ = predominant localization.

TABLE 2

| SAMPLE NO. | TUMOR DESCRIPTION | REACTIVITY WITH ANTI-PS1 |
|---|---|---|
| UB 2102 | Uterine tumor | Negative |
| PN 2376 | Uterine tumor | Negative |
| SB 0379 | Perivaginal tumor | Negative |
| SS 0688 | Vulva tumor | Negative |
| VM 9758 | Omentum* tumor | +++ |

*Omentum tumor from patient having metastatic adenocarcinoma of ovary

EXAMPLE 3

SPECIFICITY OF ANTI-OSE ANTIBODY TO OVARIAN CANCER TISSUE

Tumors were obtained and analyzed as described for Example 2 for binding of the anti-OSE antibody, PS1. As shown in Table 2, non-ovarian tumor tissue did not react positively with the PS1 antibody. In contrast, an omentum tumor taken from a patient diagnosed with metastic adenocarcinona of the ovary was highly reactive with the PS1 antibody. These results demonstrate the use of anti-OSE antibodies to characterize metastatic tumors as having an ovarian origin.

EXAMPLE 4

PS1 BINDS AN ANTIGEN SECRETED BY OSE

Both ovaries were removed from a mature (>14 weeks) New Zealand White rabbit, trimmed, and placed into warm PBS, pH 7.2. The ovaries were rinsed three times in Hank's Balanced Salt Solution (HBSS) (GIBCO) and placed into a 25 ml Erlenmeyer flask containing 5 ml Dulbecco's Modified Eagle Media (DMEM) without methionine (Met-free medium) (GIBCO), 37° C. The flask was gassed for 15 minutes in a 37° C. incubator at 5% $CO_2$, then stoppered and moved to a 37° C. shaker-incubator and swirled gently at 70–80 rpm for 45 minutes.

The ovaries were next removed to a second Erlenmeyer flask containing medium as described above but also containing 100 uCi of $^{35}$S-Translabel (Met:Cys 14:3) (ICN, Irvine, Calif.). The 15 minute gassing, 45 minute swirling incubations described above were repeated four times. The medium was removed and concentrated five times using a Centricon microconcentrator having a 10,000 MW cut-off and centrifuging at 5000–6000 rpm at 4° C.

The resulting concentrated medium was assayed by immunoprecipitation with the monoclonal antibody, PS1. To eliminate non-specific binding, 25 ul of normal rabbit serum was added to 200 ul of the concentrated medium, and the samples were agitated on a platform rocker for one hour at room temperature. To this mixture was added 50 ul of a 10% suspension of Protein A Sepharose CL-4B (Pharmacia) suspended in NP-NET buffer. The samples were rocked for two hours at room temperature, or overnight at 4° C., then centrifuged at 12,000–13,000 rpm for ten minutes, and the supernatant removed.

To the adsorption-treated supernatant was added 100 ul of PS1 antibody (1.6 mg/ml protein) and the samples were rocked for two hours at room temperature (or overnight at 4° C.). After incubation with PS1, 50 ul of affinity purified rabbit anti-mouse IgG (1 mg/ml protein) was added and the samples were again rocked for one hour at room temperature. A volume of 100 ul of the 10% suspension of Protein A-Sepharose in NP-NET described above was added to each sample which was then vortexed briefly and rocked for two hours at room temperature or overnight at 4° C. The samples were then centrifuged at 12,000–13,000 rpm for ten minutes and the supernatant removed. The pellet containing PS1-bound $^{35}$S-labeled proteins was washed twice in NP-NET buffer and analyzed by SDS-polyacrylamide gel electrophoresis (PAGE).

To each sample pellet was added freshly made SDS solubilization buffer (0.0625 M Trizma base containing 10% glycerol and 2% SDS to which 2–5% beta-mercaptoethanol was added immediately prior to use). The mixture was heated in a boiling water bath for ten minutes, cooled to room temperature, centrifuged at 12,000–13,000 rpm for ten minutes and the supernatant removed for electrophoresis.

One dimensional PAGE was performed using conventional procedures. A 10% polyacrylamide gel was prepared, and samples added to lanes and electrophoresed. The resulting gel was stained with Coomassie blue stain, destained in ethanol/acetic acid, and treated with 1X EN$^3$HANCE reagent (Dupont) for one hour with gentle agitation. The reagent was discarded and the gel was washed with deionized water for 30 minutes. The washed gel was dried and placed against X-ray film for the production of autoradiographs. Development of the film overnight at −70° C. was generally sufficient for the production of a strong signal.

Figure 5:
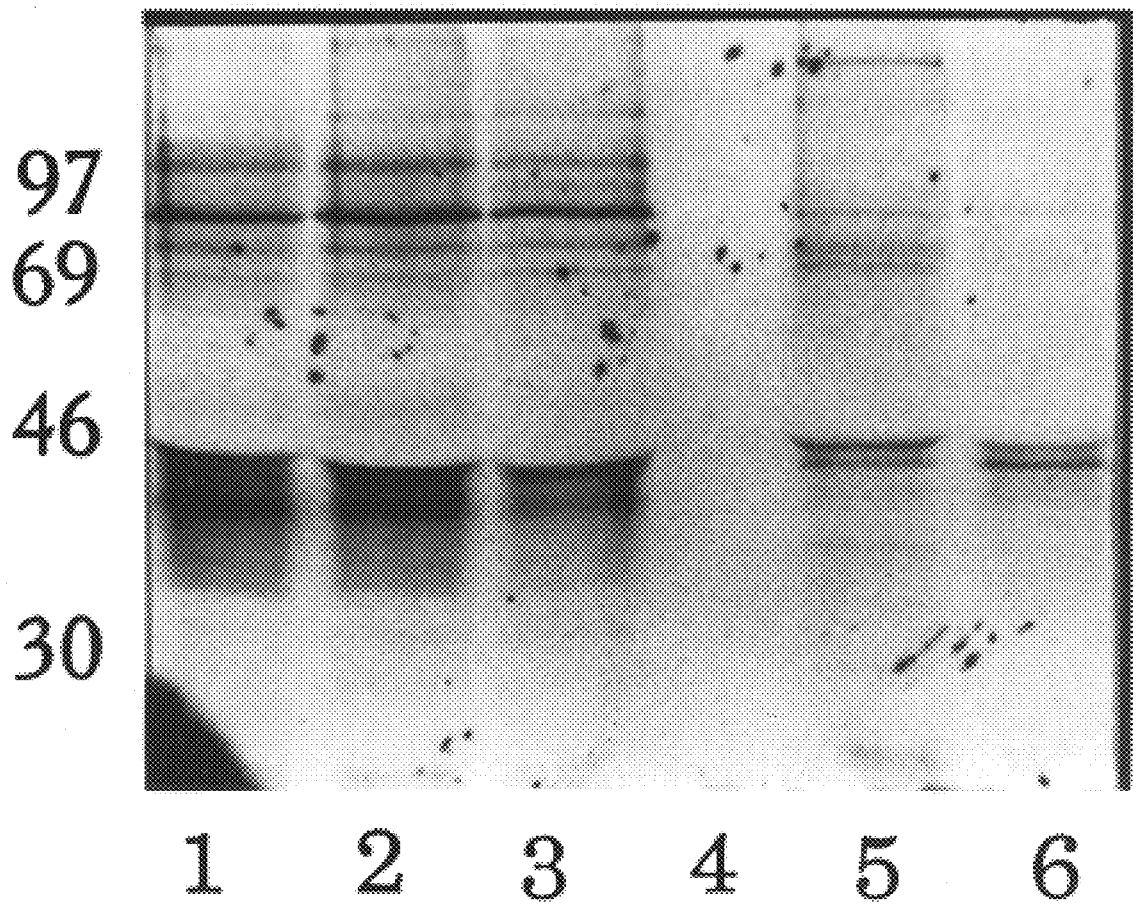
FIG. 5 shows an autoradiograph of proteins radiolabeled with $^{35}$S-Translabel, secreted by rabbit OSE in vitro, immunoprecipitated with anti-PS1 antibody, and electrophoresed in 7.5% polyacrylamide. Lanes 1–3 contain OSE secretory proteins.

The resultant autoradiograph is shown in FIG. 5. Lanes 1–3 contained proteins immunoprecipitated from the conditioned medium of the ovaries incubated as described above. These proteins may be presumed to be secreted predominantly by the ovarian surface epithelium cells and not other ovarian cell types because of the short incubation period. Only cells at the surface of the ovary are expected to take up the labeled amino acids, incorporate label into protein, and release labeled protein into the culture medium in such a short time. The OSE cells are those available to the label on the surface of the ovary. Lane 4 contained molecular weight markers. Lane 5 contained cytoplasm of isolated OSE cells and Lane 6 plasma membranes isolated from OSE after labeling as described above.

EXAMPLE 5

IDENTIFICATION OF ANTIGENS SECRETED BY OSE

Antigens secreted by the OSE are useful for the production of antibodies for the detection of tissue and secreted antigens conserved in ovarian tumor cells. Such antigens may be prepared and screened, for example, by the following procedure.

OSE is isolated from the ovaries of a mammal, e.g, rabbit, as adapted from Nicosia et.al, *International Journal of Gyn. Path.*, 1984, 3:348–360. Ovaries are rinsed three times briefly in HBSS at 37° C. and placed into a 50 ml plastic centrifuge tube containing 10 ml dissociation solution (10 ml Medium 199 containing 3000 units of collagenase, 25 units/ml penicillin and 50 ug/ml streptomycin, the final mixture filtered through a 0.22 u filter before use and at 37° C.). The sample is gassed for 15 minutes at 5% $CO_2$ and 37° C., then stoppered and moved to a 37° C. shaker-incubator and swirled gently (70–80 rpm) for 45 minutes.

After dissociation, the contents of the tube are poured into a plastic petri dish and the ovaries gently lifted into a 15 ml plastic centrifuge tube containing 10 ml Medium 199 at 37° C. The solution is aspirated gently five times with a Pasteur pipette, and then vortexed. The solution is then gently aspirated again five times, and the contents poured onto a watch glass. The ovary is immobilized with a needle placed through its long axis and the surface of the ovary is gently scraped with a scalpel blade, releasing the OSE into the solution.

The ovaries are then removed and the solution containing the OSE is placed into a 15 ml plastic centrifuge tube and centrifuged at 1400 rpm for five minutes. The supernatant is discarded and the pellet resuspended in 3 ml Medium 199 at 37° C. The solution is then layered onto a 10 ml "unit gradient" (5% BSA in Medium 199, pH 7.2, sterile filtered) and allowed to sit undisturbed for twenty minutes.

All but the lower 3 ml of the "gradient" is pipetted off and discarded. The remaining 3 ml is centrifuged at 1400 rpm for 5 minutes, the resulting supernatant is discarded, and the pellet washed twice with 10 ml HBSS at room temperature, and again centrifuged.

The OSE cells are then cultured by means known in the art, for example, using conditions as described in Maresh et al, 1990, *Biol. Reprod.*, 43:965–976. The conditioned medium is then collected from the OSE cultures and proteins concentrated, for example, using the diatomaceous earth procedure described by Dunbar, 1987, in *Two Dimensional Electrophoresis and Immunological and Immunological Techniques*, p. 223–225.

The OSE secreted proteins are analyzed by two-dimensional gel electrophoresis, by methods known in the art. See, for example, Dunbar, 1987, *Two Dimensional Electrophoresis and Immunological Techniques*, Plenum Press, New York. Proteins detected by staining, i.e., Coomassie blue or silver stain, are isolated from the polyacrylamide gel using procedures known in the art (see Dunbar, 1987) and used to inject animals to prepare polyclonal and monoclonal antibodies (see Dunbar, 1987).

The PS1 antibody can be used to immunoprecipitate secreted OSE proteins, as described in Example 3 above. Proteins identified using this procedure may be separated by two-dimensional PAGE and purified for use as antigens to prepare anti-OSE antibodies.

Efficacy of anti-OSE antibodies prepared as described herein for utility as ovarian cancer markers can be tested by the antibody's recognition of ovarian tumor tissue using the immunohistochemical procedures described in Example 2, as well as identification of antigens secreted by human ovarian cancer cell lines. Secretion of antigen into the body fluids and or circulation in the blood may be evaluated using conventional immunoassay techniques, e.g., competitive ELISA procedures.

EXAMPLE 6

TARGETING OF THERAPEUTIC AGENTS

Therapeutic agents may be conjugated to anti-OSE antibodies for targeted delivery to ovarian cancer tissue. For example, cytotoxic agents including radioisotopes and cytotoxins such as ricin may be conjugated by means known in the art to anti-OSE antibodies.

The specific binding of the anti-OSE antibody to ovarian cancer cells enables specific delivery of the agent to the cancer tissue.

I claim:

1. A method of targeted delivery of a therapeutic agent to ovarian cancer tissue comprising the steps of:

conjugating a therapeutic agent to PS1 antibody secreted by hybridoma cells having ATCC Accession number HB9566; and administering the conjugated antibody to a patient.

* * * * *